(12) United States Patent
Neynavaee et al.

(10) Patent No.: US 10,088,462 B2
(45) Date of Patent: Oct. 2, 2018

(54) GAS SAMPLING DEVICE

(71) Applicant: Google Inc., Mountain View, CA (US)

(72) Inventors: Houtan Neynavaee, San Jose, CA (US); Stephen Theodore Schooley, Menlo Park, CA (US); Sam Kavusi, Menlo Park, CA (US)

(73) Assignee: Google LLC, Mountain View, CA (US)

( * ) Notice: Subject to any disclaimer, the term of this patent is extended or adjusted under 35 U.S.C. 154(b) by 189 days.

(21) Appl. No.: 15/274,950

(22) Filed: Sep. 23, 2016

(65) Prior Publication Data

US 2017/0089873 A1 Mar. 30, 2017

Related U.S. Application Data

(60) Provisional application No. 62/235,261, filed on Sep. 30, 2015.

(51) Int. Cl.
| | | |
|---|---|---|
| *G01N 33/00* | (2006.01) | |
| *G01N 1/22* | (2006.01) | |
| *G06K 9/46* | (2006.01) | |
| *A61M 15/00* | (2006.01) | |

(52) U.S. Cl.
CPC ....... *G01N 33/0001* (2013.01); *G01N 1/2273* (2013.01); *G01N 33/0006* (2013.01); *G01N 33/0062* (2013.01); *G06K 9/4652* (2013.01); *G01N 2033/0068* (2013.01)

(58) Field of Classification Search
CPC ......... G01N 1/2273; G01N 2033/0068; G01N 33/0001; G01N 33/0006; G01N 33/0062; G06K 9/4652
See application file for complete search history.

(56) References Cited

U.S. PATENT DOCUMENTS

2016/0018373 A1* 1/2016 Page .................... G01N 1/2273
436/55
2016/0363570 A1* 12/2016 Blackley ............ G01N 33/0006

* cited by examiner

*Primary Examiner* — Jennifer Wecker
(74) *Attorney, Agent, or Firm* — Colby Nipper

(57) ABSTRACT

This document describes a gas sampling device. The gas sampling device is capable of housing sensors printed on thin film (e.g., paper) and is operable to expose the sensors printed on the thin film to air for a brief period of time to sample the air for smells. The exposure causes a chemical reaction between the sensors and the sampled air and differs depending on the smells of the sampled air. After exposure, an image of the reacted sensor is captured. The image is analyzed according to image processing techniques to recognize the smells of the sampled air. The gas sampling device is also capable of concurrently sampling air from a surrounding environment along with sampling air from a specimen of interest. By analyzing both samples, the smells of the specimen of interest can be distinguished from those of the surrounding environment. Once the smells are ascertained, a profile of chemical groups in gases of the sampled air is output.

20 Claims, 13 Drawing Sheets

GAS SAMPLING DEVICE

RELATED APPLICATION

This application claims priority under 35 U.S.C. § 119 to Provisional Application No. 62/235,261, titled "Gas Sampling Device" and filed on Sep. 30, 2015, the entire disclosure of which is incorporated by reference herein.

BACKGROUND

Smell is the faculty or power of perceiving an odor or scent of something In humans, smells are perceived when odorant molecules bind to specific sites on olfactory receptors—membrane proteins contained in specialized sensory cells of the nasal cavity used to detect the presence of smell. In comparison to other animals, humans have a lesser proportion of these cells relative to certain respiratory cells, resulting in a less keen sense of smell than many animals. This less keen sense of smell inhibits many people from recognizing whether food is spoiled, determining what ingredients are in food, deciphering smells from certain beverages, and so on. Of more serious consequence though, humans' less keen sense of smell can inhibit them from recognizing dangerous conditions, such as gas leaks, the presence of carbon monoxide, the presence of predatory animals, and so on.

Due at least in part to this deficiency in detecting smells, efforts have been made to develop technologies capable of detecting smells. One such example is gas sensing technology, which is utilized for gas detection. Gas sensing technology has been limited in its performance, however, because it suffers from a variety of drawbacks such as poor ability to discriminate between gases (e.g., volatile organic compounds), sensitivity to humidity, high power consumption (e.g., can involve a 500 degree Fahrenheit temperature to operate), and so on. Conventional smell detecting techniques are also limited to pattern recognition on an array of weak chemical bonds. The drawbacks of conventional smell detecting devices and techniques render them unsuitable for widespread use in consumer and medical applications.

SUMMARY

This document describes a gas sampling device. The gas sampling device is capable of housing sensors printed on thin film (e.g., paper) and is operable to expose the sensors printed on the thin film to air for a brief period of time to sample the air for smells. The exposure causes a chemical reaction between the sensors and the sampled air and differs depending on the smells of the sampled air. After exposure, an image of the reacted sensor is captured. The image is analyzed according to image processing techniques to recognize the smells of the sampled air. The gas sampling device is also capable of sampling air from a surrounding environment concurrently with sampling air from a specimen of interest. By analyzing both samples, the smells of the specimen of interest can be distinguished from those of the surrounding environment.

Through analysis of the reacted sensors, patterns can be recognized for an array of relevant strong chemical bonds that cause color change in dyes printed on a thin film (e.g., paper), such as acids, bases, redox resulting from redox reactions in which one molecule or substance is reduced and another is oxidized, metalloporphyrins, and so on. This pattern recognition enables the techniques involving the gas sampling device to differentiate between different types of coffee as well as different types of bacteria. Additionally, this pattern recognition enables the techniques involving the gas sampling device to recognize smells indicative of various medical conditions, such as asthma, diabetes, lung cancer, oxidative stress, and so on. Once smells are ascertained, a profile of chemical groups in gases of the sampled air is output. The components of the gas sampling device (e.g., the sensors printed on the thin film, image capturing components, and so on) as well as the techniques used to analyze the reacted sensors enable the gas sampling device to be deployed for a variety of consumer and medical applications.

This summary is provided to introduce simplified concepts concerning the techniques, which are further described below in the Detailed Description.

BRIEF DESCRIPTION OF THE DRAWINGS

Embodiments of a gas sampling device and techniques involved in its use are described with reference to the following drawings. The same numbers are used throughout the drawings to reference like features and components.

DETAILED DESCRIPTION

Overview

Figure 1:
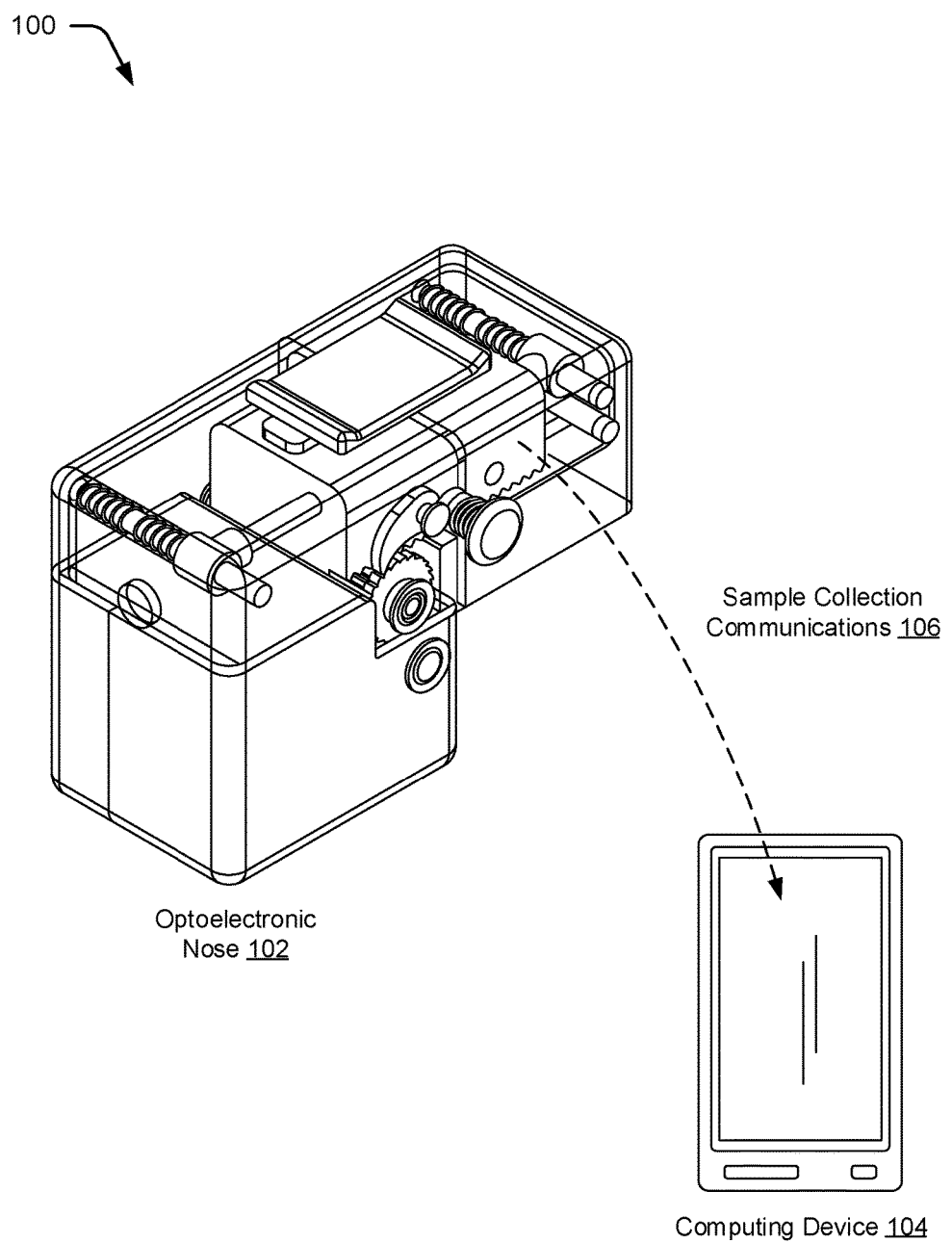
FIG. 1 illustrates an example environment in which the techniques can be implemented.

This document describes techniques using, and examples of gas sampling devices. Through use of these techniques and devices, smells in air samples can accurately be ascertained at a cost that renders these techniques and devices suitable for a wide variety of applications, including various consumer applications (e.g., detecting spoiled food, ingredients in food, recognizing smells in coffee, and so on) and medical applications (e.g., detecting asthma, diabetes, lung cancer, oxidative stress, and so on). As used herein, the term "smell" refers to the presence of chemicals in an air sample that are capable of being profiled, such as how much of a particular chemical is in the air sample, a list of chemical compounds, and so forth. This contrasts with conventional smell detecting devices and techniques which have drawbacks that render them unsuitable for such uses, such as poor ability to discriminate between gases (e.g., volatile organic compounds), sensitivity to humidity, high power consumption (e.g., can involve a 500 degree Fahrenheit temperature to operate), and so on.

By way of example, a person can interact with the gas sampling device by holding the device near a specimen that is to be sampled (e.g., food, a cup of coffee, a glass of wine, etc.) and then pushing a button to initiate smell detection. Once initiated, sensors housed within the gas sampling device are positioned for exposure to air proximate the specimen of interest. The air sample is collected by the gas sampling device and exposed to the sensors. The exposed sensors are then analyzed to determine what smells are in the air sample. In another example, the gas sampling device collects two different samples, one through one end of the gas sampling device and a second through another end of the gas sampling device. One of these two samples can be of air in the environment that surrounds the gas sampling device while the other is of the particular specimen to be sampled. By collecting the two samples the smells in the air can be distinguished from the smells of the specimen, resulting in a more accurate profile of the smells in the specimen.

Consider an example in which the multi sample technique is used for determining smells in a person's breath. While one end of the gas sampling device is held up to a person's mouth, another end can be exposed to air in the environment surrounding the gas sampling device. Upon initiation of smell detection (e.g., by pushing a button of the gas sampling device or by a computing device interacting with the gas sampling device), the sensors housed within the gas sampling device are positioned for exposure to air sampled from the person's breath and the surrounding environmental air. The air from the person's breath and surrounding environment is then collected and exposed to the sensors. The exposed sensors are then analyzed to determine what smells are in both the person's breath as well as the surrounding environmental air. Based on the differences, the smells in the person's breath can be determined with relative accuracy. Once the analysis is performed and the smells are ascertained, an indication of the smells (e.g., a profile of chemicals in the air) can be output, such as via a computing device with which the gas sampling device interacts.

These are but a couple simple examples of ways in which the techniques using the gas sampling device can be performed, other examples and details are provided below. This document now turns to an example environment, after which example devices and methods for implementing gas sampling device techniques, and an example computing system are described.

Example Environment

FIG. 1 is an illustration of an example environment 100 in which techniques using a gas sampling device can be employed. Environment 100 illustrates a gas sampling device referred to hereinafter as optoelectronic nose 102 as well as computing device 104 that can interact with the optoelectronic nose 102 to ascertain smells in collected air samples. The optoelectronic nose 102 can be configured as a peripheral device of the computing device 104. In some cases, the computing device 104 receives sample collection communications 106 from the optoelectronic nose 102 to aid in ascertaining the smells of the collected air samples. In the particular example of FIG. 1, the computing device 104 is configured as a smartphone, however, other configurations are contemplated. Other configurations of the computing device 104 for interacting with the gas sampling device to ascertain smells in collected air samples are illustrated in later figures.

Sample collection communications 106 are communicable from the optoelectronic nose 102 to other entities, such as the computing device 104, other computing devices remote from the computing device (not shown), and so on. The sample collection communications 106 can include data that enables the optoelectronic nose 102 to interact with the computing device 104 to ascertain the smells in collected air samples, such as timing information, images captured by the optoelectronic nose 102 of reacted sensors printed on thin film (e.g. paper), indications for the computing device 104 to capture images of the reacted sensors, notifications that the optoelectronic nose 102 is ready to collect a next air sample, indications to activate applications of the computing device 104, alarms for such applications, and so forth. Given this, the images of the reacted thin-film sensors can be communicated to the computing device 104, where image processing techniques used to analyze the captured images can be applied and the smells in the air samples ascertained. By doing so, the computing burden of ascertaining smells from captured images of the reacted thin-film sensors can be offloaded from the optoelectronic nose 102.

Figure 2:
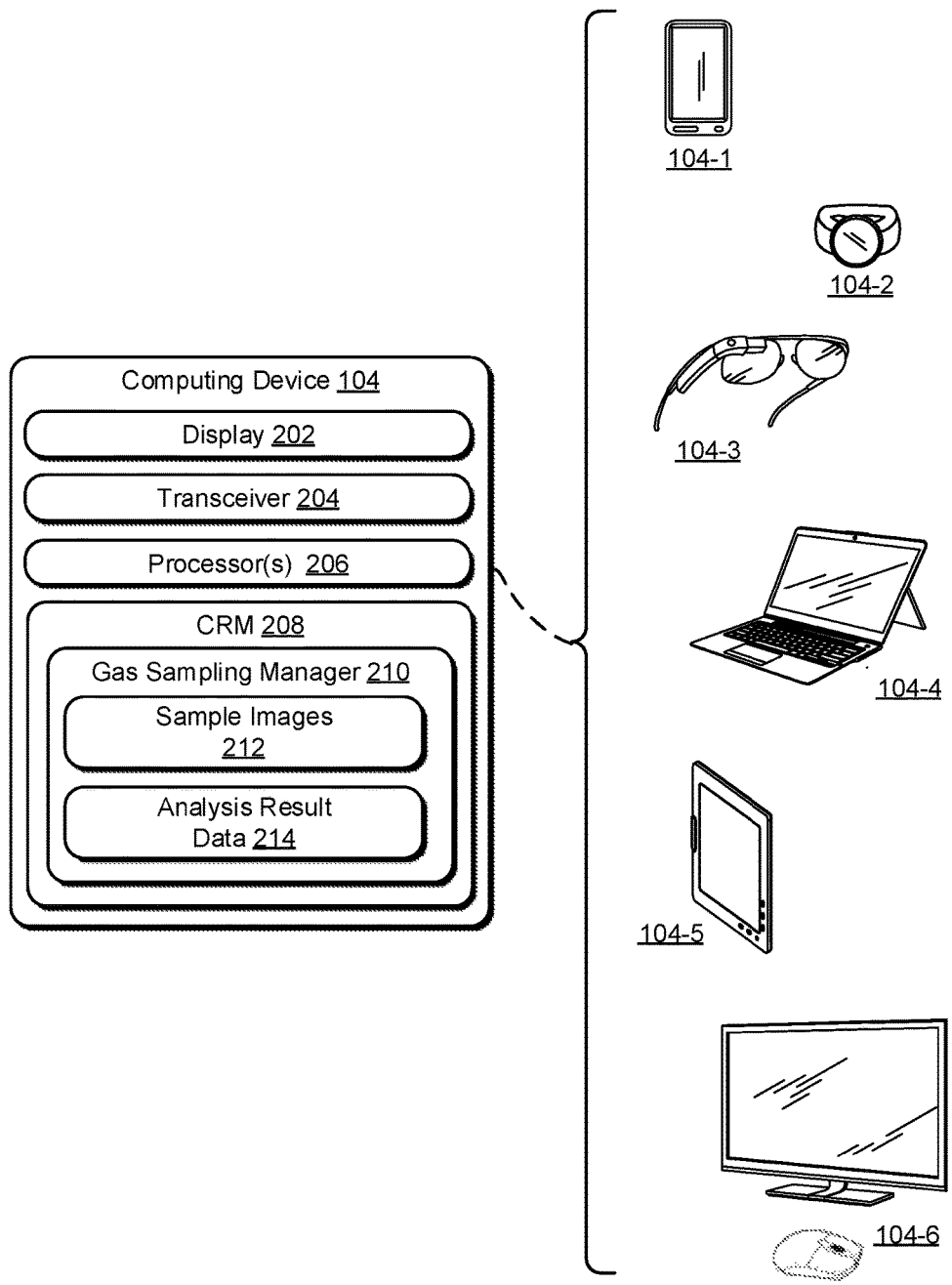
FIG. 2 illustrates an example computing device of FIG. 1 configured interact with the gas sampling device of FIG. 1 to analyze sampled air and ascertain smells of the sampled air.

With regard to the example computing device 104 of FIG. 1, consider a detailed illustration in FIG. 2. The computing device 104 can also be implemented as one or a combination of various devices, here illustrated with six examples: a smartphone 104-1, a computing watch 104-2, computing spectacles 104-3, a laptop 104-4, a tablet computer 104-5, and a desktop with a mouse 104-6, though other computing devices and systems, such as a netbook, or a set-top box may also be used. As noted above, in some embodiments the techniques operate, in whole or in part, through a remote device. The remote computing device can be configured as a server, for example. In such cases, some computing can be forgone locally, e.g., through a communication device having limited computing operations or even directly from devices 104 to the server.

The computing device 104 includes or is able to communicate with a display 202 (six are shown in FIG. 2), a transceiver 204, one or more processors 206, and computer-readable storage media 208 (CRM 208). The transceiver 204 is capable of sending and receiving data directly or through a communication network, such as the sample collection communications 106 from the devices 104 through a local area, wide area, personal area, cellular, or near-field network, e.g., the Internet, Bluetooth®, and so on. The optoelectronic nose 102 includes one or more communication devices capable of sending and receiving data directly or through a communication network such as the sample collection communications 106 from the devices 104 through a local area, wide area, personal area, cellular, or near-field network, e.g., the Internet, Bluetooth®, and so on.

The CRM 210 includes gas sampling manager 210, which includes or has access to sample images 212 and analysis result data 214. The sample images 212 are captured of the reacted thin-film sensor, and can be captured by imaging functionality of the optoelectronic nose 102 and communicated to the computing device 104 for processing, or can be captured by imaging functionality of the computing device 104. The computing device 104 is capable of capturing the sample images 212 of the reacted thin-film sensors responsive to an indication from the optoelectronic nose 102 to do so. By way of example, the optoelectronic nose 102 can communicate an indication via the sample collection communications 106 to use imaging functionality of the computing device 104 to capture the sample images 212. Responsive to receipt of this indication, the computing device 104 can output a notification indicating to position the computing device 104 relative the optoelectronic nose 102 to capture a sample image. Once positioned, the computing device 104 can capture an image of the reacted to sample using imaging functionality. The indication instructing the computing device 104 to capture the sample images 212 may be communicated after an exposure time lapses that allows chemical reactions to occur between the thin-film sensor and the collected air samples. Alternately, the indication may be communicated to the computing device 104 prior to the exposure time lapsing, and the computing device 104 may wait until the exposure time lapses to capture the sample images 212.

By "positioned" it is meant that the computing device 104 is placed relative the optoelectronic nose 102 in a manner that enables imaging functionality (e.g., a camera) of the computing device 104 to capture an image of the reacted thin-film sensor. The computing device 104 may be positioned relative the optoelectronic nose 102 using mechanical means, e.g., the computing device may attach to or within the optoelectronic nose 102. Alternately or in addition, an application of the computing device 104 may aid in positioning the computing device 104 relative the optoelectronic nose 102 for capturing images of the reacted thin-film sensor, such that a display of the computing device 104 guides a user with directions as to which way to move the computing device 104 so that a camera lines up with the reacted thin-film sensor to capture an image of it.

The gas sampling manager 210 represents functionality of the computing device to process the sample images 212 to ascertain smells in the air samples captured by the optoelectronic nose 102. To ascertain the smells, the gas sampling manager 210 applies one or more image processing techniques to the sample images 212 to analyze them. Broadly speaking, the sample images 212 capture how thin-film sensors react when exposed to an air sample for an exposure time, e.g., an amount of time that allows chemical reactions to occur between a sensor and collected air samples. In addition to or instead of human-visible information, the images captured may capture non-visual information about the chemical reactions, such as infrared, ultraviolet, and so on. Exposure to an air sample causes a chemical reaction with the sensors, which differs visibly depending on the smells of the sampled air and may also differ in terms of other characteristics, such as heat emitted. In other words, the chemical reaction causes the sensors to exhibit different visual and non-visual characteristics depending on the smells of the sampled air. By analyzing the sample images with the one or more image techniques, the gas sampling manager 210 is capable of recognizing the smells in sampled air. For instance, the gas sampling manager 210 is capable of pattern recognition for an array of relevant strong chemical bonds that cause color change in dyes printed on a thin film (e.g., paper), such as acids, bases, redox resulting from redox reactions in which one molecule or substance is reduced and another is oxidized, metalloporphyrins, and so on. In one or more implementations, the analysis involves the sampling manager 210 matching the characteristics captured in the images (visual and/or non-visual) to known patterns indicative of particular smells.

Once the smells of the sampled air are ascertained, the gas sampling manager 210 generates the analysis result data 214, which indicates the ascertained smells of the sampled air. The analysis result data 214 can be used to present a user with a variety of information. For example, the analysis result data 214 can indicate a profile of the chemical groups in the gases (one molecule can have multiple groups) of the sampled air. The analysis result data 214 can also be used to indicate the presence or absence of particular smells, which can indicate the presence or absence of certain conditions, such as medical conditions, spoilage in food, alcohol on a person's breath, harmful gases, and so on. Further, the analysis result data 214 can be used to present a list of the smells ascertained, such as ingredients in food (e.g., which can help prevent someone with allergies from eating food containing allergens, can help reverse engineer the food to derive a recipe, and so on), smells that result from brewing, curing, or fermenting (e.g., smells in beer, coffee, wine, and so on). In one or more implementations, the analysis result data 214 can also be used to indicate a person's blood alcohol content (BAC). In addition to the examples enumerated, the analysis result data 214 can be used to indicate a variety of other smells without departing from the spirit or scope of the techniques described herein. Furthermore, in contrast to conventional techniques, which can be deceived easily as to the smells in air samples because they lack specificity (e.g., missing most dimensions in chemical groups), the techniques employing the optoelectronic nose 102 are not easily deceived because of an increased level of specificity—resulting in a higher degree of accuracy with regard to the smells ascertained in air samples.

Figure 3:
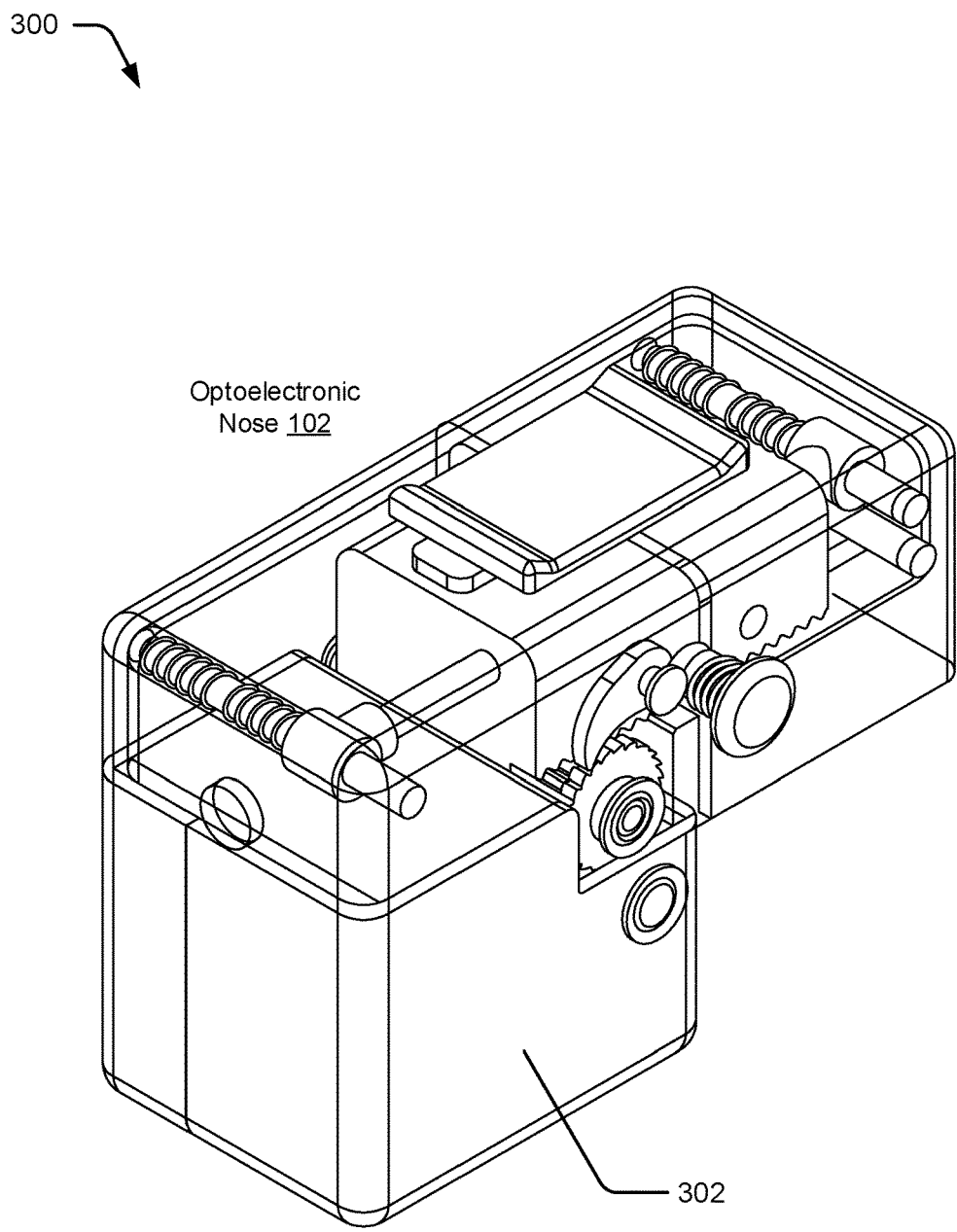
FIG. 3 illustrates an example gas sampling device of FIG. 1 configured to house gas sampling sensors and operational to expose the gas sampling sensors to air samples.

FIG. 3 illustrates the optoelectronic nose 102 of FIG. 1 in an expanded view. The optoelectronic nose 102 includes sensor housing 302, which is capable of housing gas sampling sensors. In one or more implementations, the gas sampling sensors used in the optoelectronic nose 102 are paper sensors. As will be discussed in more detail below, the optoelectronic nose 102 is operable (e.g., responsive to application of a trigger) to peel a top paper wrap from the paper sensors, place a peeled sensing portion in a position to be exposed to an air sample, obtain air samples (e.g., by sucking them into the optoelectronic nose) to expose the peeled sensing portion (resulting in one or more chemical reactions between the peeled sensing portion and the air sample), capture images of the reacted peeled sensing portion, and communicate the captured images to the computing device 104. In addition or alternately, some of that functionality can be offloaded to the computing device, such as capturing images of the reacted peeled sensing portion. By way of example, the optoelectronic nose 102 is also capable in one or more implementations of communicating to the computing device 104 an indication that indicates to capture an image of the reacted paper sensor. Accordingly, the computing device 104 can then capture the image of the reacted sensor instead of the optoelectronic nose 102.

With regard to the sensor housing 302, it is configurable to house at least one of thin-film gas sampling sensors or gas sensors in chip format. Although the "thin-film" sensors are generally described herein as paper sensors for the sake of convenience, a thin film other than paper may also be used for such sensors. When configured to house thin-film gas sampling sensors, not only is the sensor housing 302 capable of storing rolls of thin-film sensors that have not yet been used, but the sensor housing may also be capable of storing the refuse from the thin-film sensors that have already been used. In addition to these capabilities, the sensor housing 302 keeps the thin-film sensors from being exposed to air before use, and can be opened to empty the used sensor refuse as well as to load new rolls of the thin-film sensors. Regarding gas sensors in chip format, these can reduce a frequency with which the sensors need to be replaced.

Figure 4:
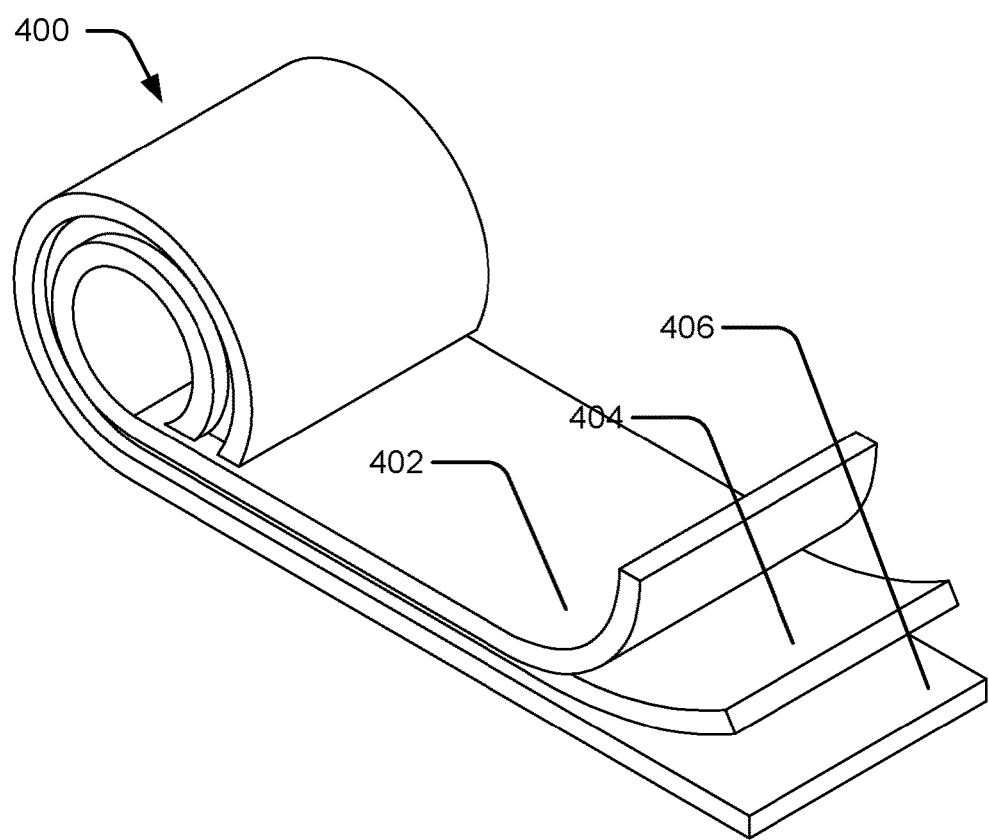
FIG. 4 illustrates an example paper sensor that the gas sampling device can expose to air samples for ascertaining smells.

FIG. 4 is an illustration of an example paper sensor 400 with which the sensor housing 302 can be loaded and which the optoelectronic nose 102 is operable to expose to air samples for detecting smells. Broadly speaking, paper sensors are printed onto a roll. In the illustrated example, the example paper sensor includes a paper cover portion 402, a sensing portion 404, and a back support plastic wrap portion 406. Until the paper cover portion 402 is peeled away, it keeps the sensing portion 404 from being exposed to air. Exposure to environmental gases before usage would change the sensing portion 404's response (e.g., chemical reaction) to an air sample. Covering the sensing portion 404 with the paper cover 402 enables the example paper sensor 400 to have a longer shelf life.

The sensing portion 404 of the example paper sensor 400 is the portion that reacts with the air samples collected by the optoelectronic nose 102, and which the optoelectronic nose 102 exposes to the air samples. The sensing portion 404 can comprise paper on which one or more dyes are printed. The dyes printed on the paper can change colors (e.g., due to chemical reactions) when exposed to air samples. Given this, the images captured of the sensing portion 404 include the color changes, which the image processing techniques can detect when applied to the images.

Using paper sensors configured as rolls, like the example paper sensor 400, provides a variety of benefits. As mentioned above, the example paper sensor 400 keeps the sensing portion 404 from being exposed to air before usage—both the paper cover portion 402 and the back support plastic wrap portion 406 serve to keep the sensing portion 404 from being exposed. The paper cover portion 402 and the back support plastic wrap portion 406 may be configured with adhesives that stick them to the sensing portion. The adhesive that sticks the paper cover portion 402 to the sensing portion 404 also allows the paper cover portion 402 to be peeled from the sensing portion, e.g., without leaving a residue that affects how the sensing portion reacts with air samples. In one or more implementations, the time result is shown between 0.1 seconds and 15 minutes. The optoelectronic nose 102 can also include an additional storage component (e.g., a storage package) for storing multiple rolls of paper sensors. An advantage of the example paper sensor 400 is that it allows the optoelectronic nose 102 to have a smaller form factor than other techniques (even with a storage package) because the paper sensors stored therein are rolled.

Figure 5:
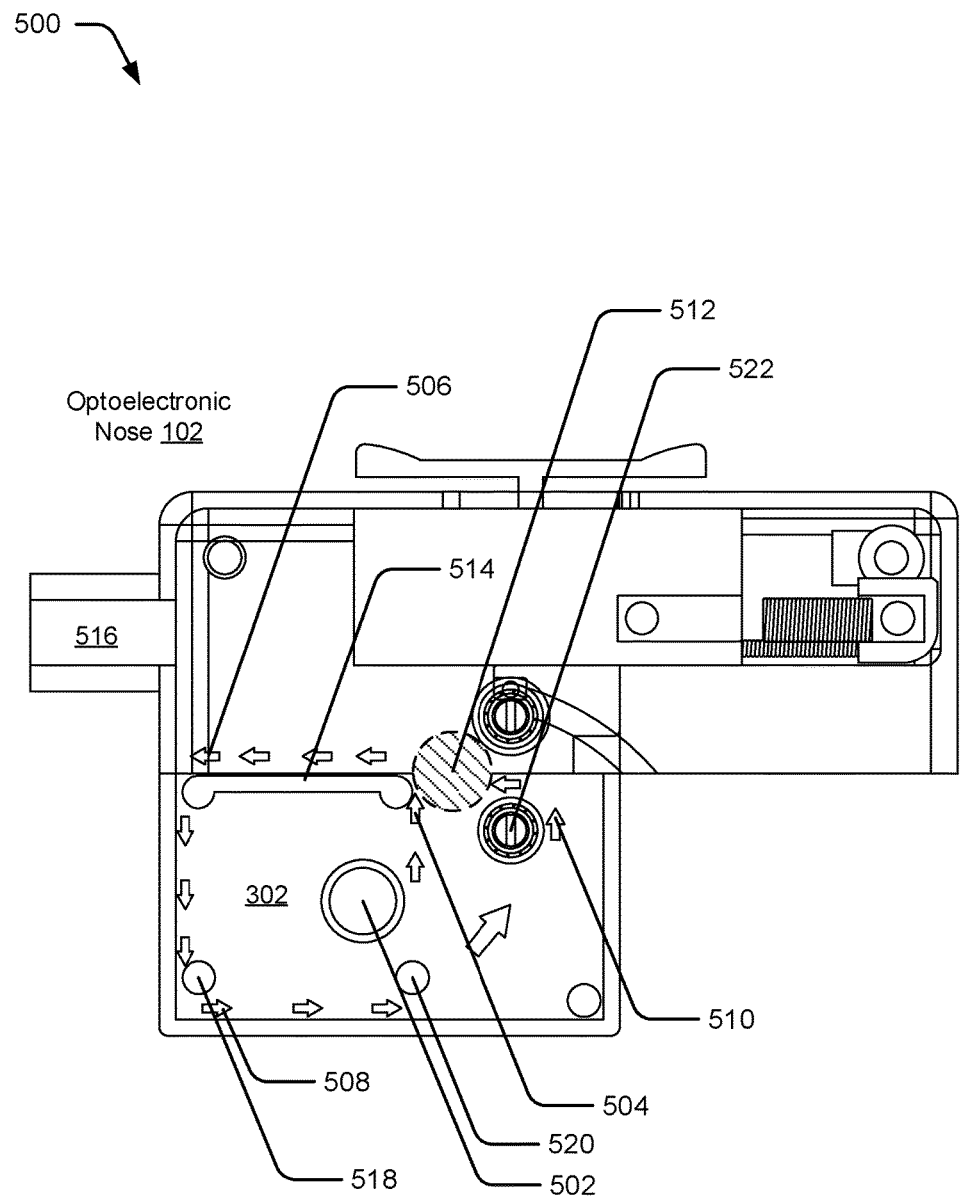
FIG. 5 illustrates an example embodiment of the gas sampling device in which gas sampling sensors printed on thin film are routed through components of the gas sampling device to expose the sensors to air samples.
Figure 6:
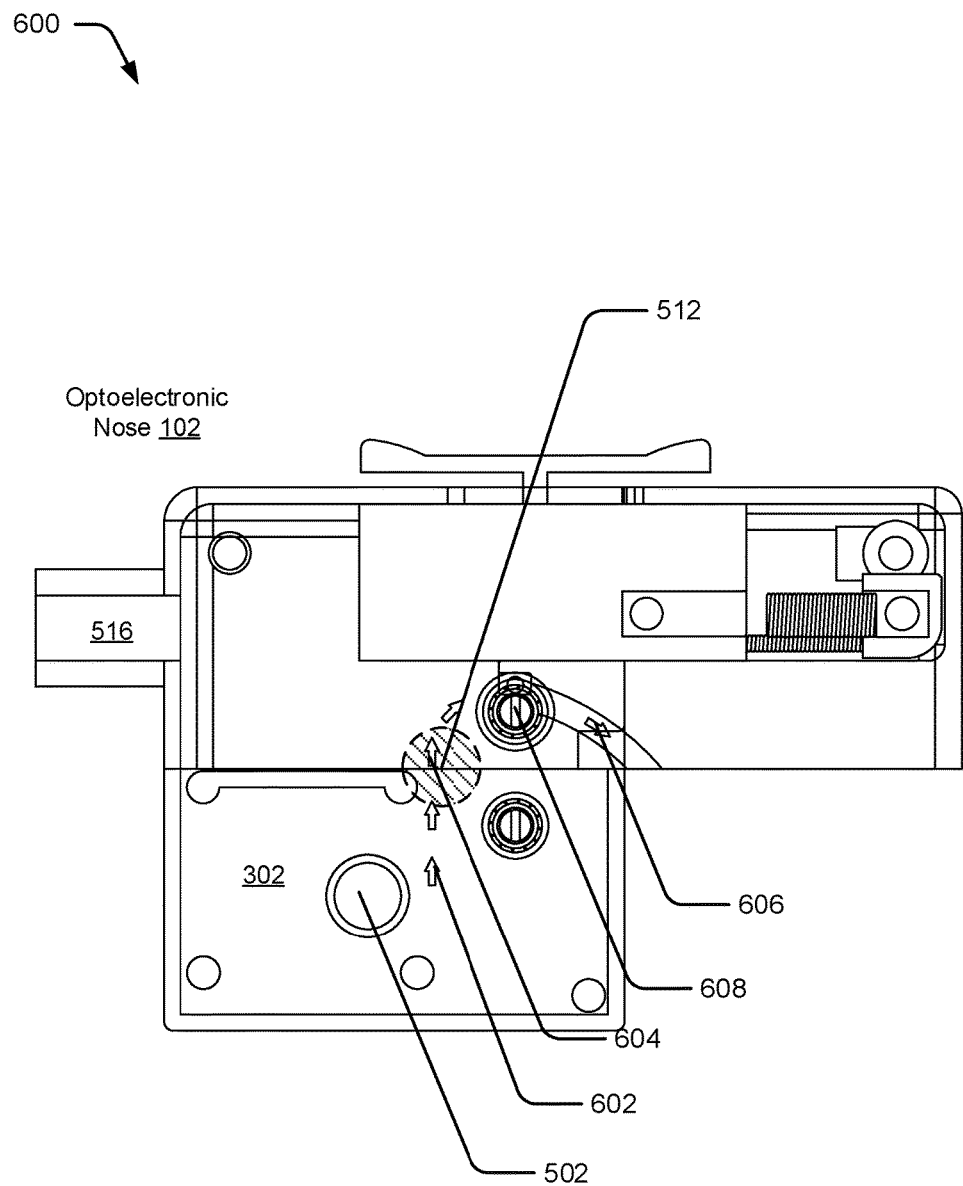
FIG. 6 illustrates another aspect of the example embodiment of FIG. 5 in which a cover portion of the gas sampling sensors is peeled from the sensors to expose the sensing portion of the sensors and is routed through components of the gas sampling device for disposal.

For context, consider FIGS. 5 and 6, which illustrate how paper sensors are routed through the optoelectronic nose 102 for sampling air. In particular, FIG. 5 illustrates how the sensing portion 404 and the back support plastic wrap portion 406 are routed through the optoelectronic nose 102. In the illustrated example, the sensor housing 302 of the optoelectronic nose 102 includes pin 502, on which a rolled paper sensor can be loaded. In operation, the paper cover portion 402 of the paper sensor is not yet peeled away from the sensing portion 404 for the length of the paper sensor that is still wound around the pin 502. The arrows, such as arrows 504, 506, 508, 510, indicate the route that the sensing portion 404 and the back support plastic wrap portion 406 take through the optoelectronic nose 102. First, the paper sensors unwind from the pin 502. At approximately area 512, the paper cover portion 402 is peeled away from the sensing portion 404 and the back support plastic wrap portion 406. From there, the sensing portion 404 and the back support plastic wrap portion 406 are routed along exposure platform 514. While disposed along the exposure platform 514, the sensing portion 404 of the paper sensors is exposed to the sampled air. Sampled air may be obtained in the optoelectronic nose 102 through airway 516. The sampled air may be sucked into the optoelectronic nose 102 through the airway 516 for instance. To do so, the optoelectronic nose 102 may be configured with a fan that enables the air samples to be sucked in through the airway 516. Although a fan is discussed herein, other manners to obtain air in the optoelectronic nose 102 may be employed without departing from the spirit or scope of the techniques described herein, such as employing an air pump.

Regardless of how the sucking is implemented, the optoelectronic nose 102 may be configured to open the airway 516 and suck in an air sample once the sensing portion 404 and the back support plastic wrap portion 406 are positioned by the optoelectronic nose 102 for exposure. The sensing portion 404 that is disposed on the exposure platform 514 is the portion of the paper sensor that is captured in the images later analyzed. From the exposure platform 514, the sensing portion 404 and the back support plastic wrap portion 406 are then routed around pins 518 and 520. The disposed sensor is rolled up on a second spring roller 522.

FIG. 6 illustrates how the paper cover portion 402 is routed through the optoelectronic nose 102. As mentioned in the discussion of FIG. 5, the paper cover portion 402 of the paper sensors is not yet peeled away from the sensing portion 404 for the length of paper sensor still wound around the pin 502. The arrows, such as arrows 602, 604, 606, indicate the route the paper cover portion 402 takes through the optoelectronic nose 102. As discussed above, the paper sensor first unwinds from pin 502. At approximately the area 512, the paper cover portion 402 is peeled away from the sensing portion 404 and the back support plastic wrap portion 406. From there, the paper cover portion 402 wraps around spring roller 608. The paper cover portion 402 is then sent out of the optoelectronic nose 102 or is disposed in the storage package (not shown). The storage package can be attached to a bottom of the optoelectronic nose 102 and, as discussed above, can be configured to store additional rolls of paper sensors. With regard to the scenario illustrated by FIGS. 5 and 6, these figures depict a scenario in which the background smells are ignored—the smells ascertained are based on a single sample collected.

Figure 7:
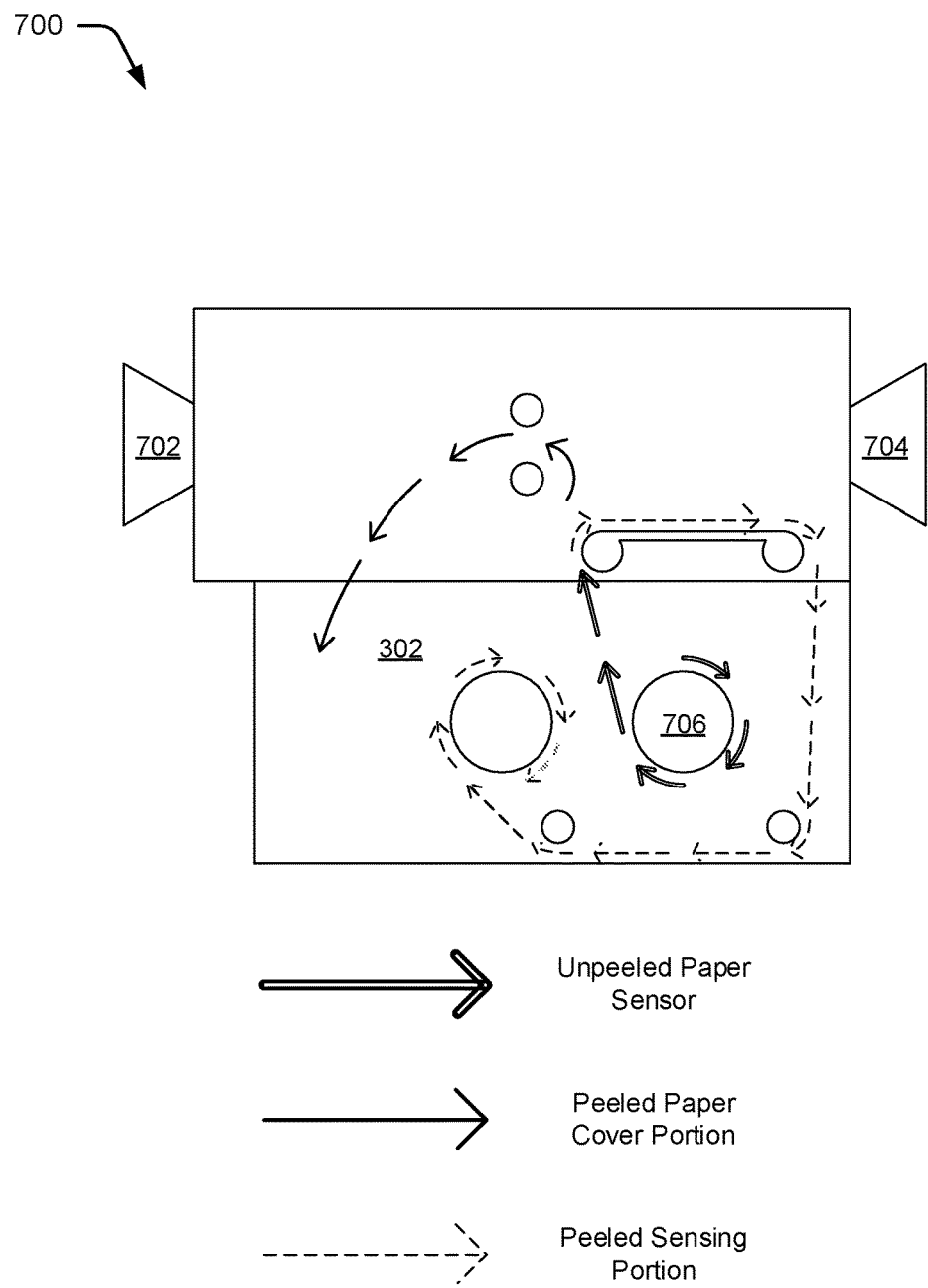
FIG. 7 illustrates another example embodiment of the gas sampling device in which it is capable of collecting two air samples at a same time, as well as an indication of how the unpeeled gas sampling sensor, the peeled cover portion, and the peeled sensing portion are routed through the gas sampling device.

In contrast, FIG. 7 illustrates an alternative embodiment in which two samples can be collected at a same time and analyzed. Unlike the optoelectronic nose 102 illustrated in FIGS. 5 and 6, the optoelectronic nose 102 illustrated in FIG. 7 includes two airways 702, 704. In operation therefore, the optoelectronic nose 102 can collect an air sample through airway 702 of surrounding environmental air and another air sample through airway 704 of breath (or some other specimen such as air emitted from food), or vice versa. The routes for the different portions of the rolled paper sensors are indicated by the different types of arrows. In this example, the route begins at pin 706. While wrapped around the pin 706, the paper cover portion 402 is not yet peeled from the sensing portion 404 and the back support plastic wrap portion 406—the hollow arrows for the unpeeled paper sensor indicate this portion of the route. The other two types of arrows are for the peeled paper cover portion (solid line arrows) and the peeled sensing portion arrows (dashed line arrows). These two types of arrows represent the routes the paper cover portion 402, and the sensing portion 404 (with the back support plastic wrap portion 406 still attached) take through the optoelectronic nose 102, respectively, once peeled apart.

The optoelectronic nose 102 and paper sensors, that are configured like the example paper sensor 400, enable the paper sensors to keep from being exposed before usage. This guarantees a longer shelf life than if the paper sensors were exposed before usage. The optoelectronic nose 102 is also capable of exposing the paper sensors to air automatically, e.g., without user interaction other than to push a trigger, or select an option on the computing device 104 to initiate smell detection. The described configuration allows for a smaller form factor of the optoelectronic nose 102 than conventional techniques. Due to the automation of the paper sensor exposure, image capturing, and analysis via image processing, the optoelectronic nose 102 reduces the possibility of human error in ascertaining smells with gas sensors, e.g., paper sensors. Additionally, the techniques described herein enable background gases (e.g., those present in a surrounding environment air sample) to be subtracted from an air sample of interest (e.g., a person's breath).

Figure 8:
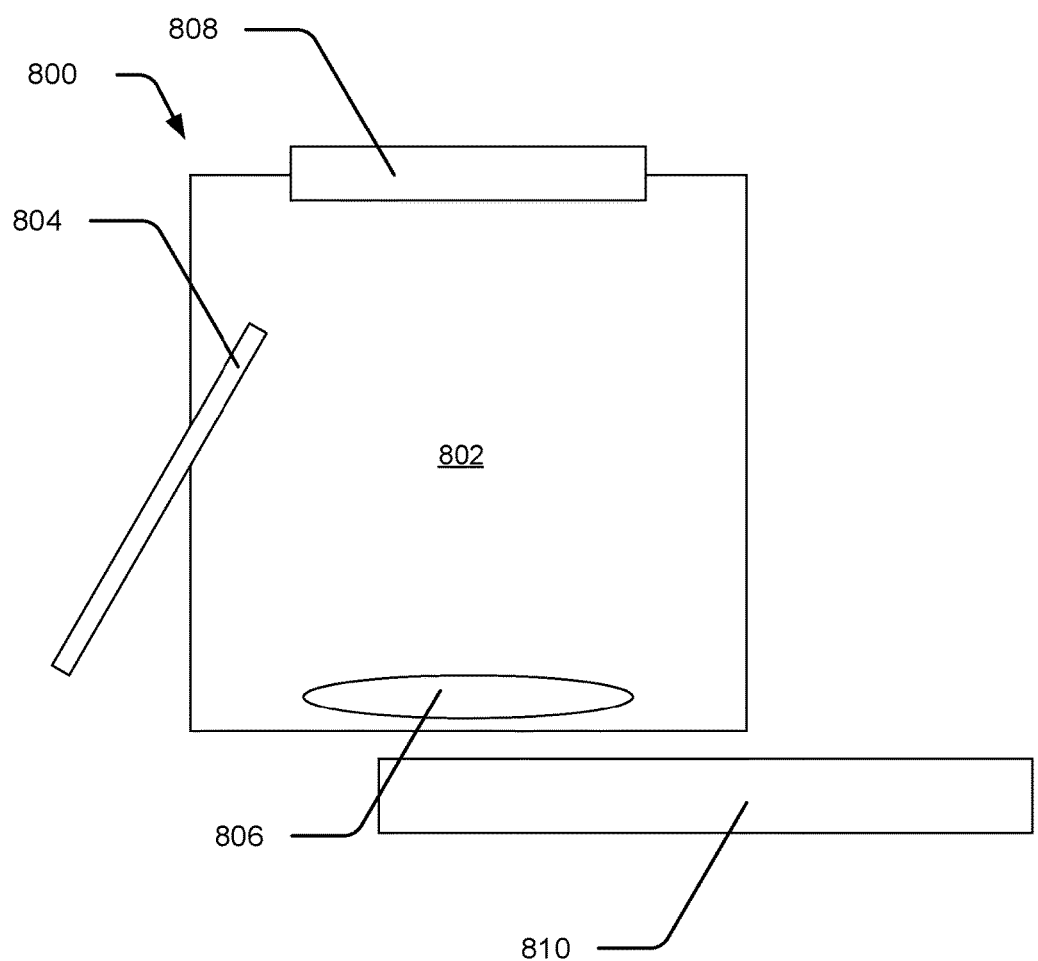
FIG. 8 illustrates an example imaging box that is implemented as part of a gas sampling device to capture images of reacted sensors.

FIG. 8 illustrates an example imaging box 800, which can be implemented as part of the optoelectronic nose 102 to aid in capturing images of reacted sensors. The example imaging box 800 includes light shielded box 802, light delivery implement 804, translation optics 806, sensor 808, and computing device 810. By way of example, the sensor 808 may correspond to any of the gas sampling sensors discussed herein, e.g., the thin-film sensors. The light shielded box 802 and the light delivery implement 804 allow control over the light to which the sensor 808 is exposed. In this way, any reactions of the dyes printed into the sensor 808 that may occur due to light exposure can be controlled. The light delivery implement 804 may be configured, for instance, as a fiber driven by one or more light emitting diodes (LEDs). The light delivery implement 804 allows for delivery on the sensor 808 of one or more types of light. The one or more types of light can include calibrated light sources, such as LED, or include narrowband light sources, such as vertical-cavity surface-emitting laser (VCSEL). The translation optics 806 are capable of translating light to adjust in some way the images that are to be captured by the computing device 810, which may correspond to the computing device 102 or imaging functionality of the optoelectronic nose 102. In one or more implementations, the translation optics 806 are configured as a macro lens although other configurations are contemplated in the spirit or scope of the techniques described herein.

With regard to additional functionality of the optoelectronic nose 102, in one or more implementations, the optoelectronic nose 102 employs filters such as desiccants, which can be disposed near airways where the air samples enter the optoelectronic nose. Such filters can alleviate condensation that can occur in the sensing area due to exposure to samples with high humidity, e.g., soup, coffee, tea aromas.

With regard to implementations in which multiple samples are collected for comparison, such as both a surrounding environment air sample and a breath air sample, calibration techniques can be applied before classifying the smells. To calibrate the optoelectronic nose 102, a background sample (e.g., the surrounding environment air sample) can be scaled and subtracted from the actual sample. Additionally or alternately, samples can be scaled to account for different exposure times. By way of example, the background sample may be exposed for a shorter amount of time, so the samples can be multiplied by the ratio of the different exposure times. Broadly speaking, the response of the dyes in the paper sensors is not linear in time. Rather, the response is exponential in time and dye dependent. To account for this, the techniques described herein are capable of maintaining and referencing a look-up table of different dyes and extrapolating the responses, e.g., using an application of the computing device 102.

With regard to additional configurations of the gas sensors, the sensors (e.g., the paper sensors) can be stamped with gaps so that the stamps are hermetically sealed thereby increasing the shelf life over non-hermetically sealed sensors. Further, the sensors can be implemented with some misregistration tolerance such that small holes are used to make it a constant distance as opposed to merely constant.

These and other capabilities, as well as ways in which entities of FIGS. 1-8 act and interact, are set forth in greater detail below. These entities may be further divided, combined, and so on. The environment 100 of FIG. 1 and the detailed illustrations of FIGS. 2-8 illustrate some of many possible environments capable of employing the described techniques.

Example Methods

FIGS. 9-12 depict methods enabling or using an optoelectronic nose. These methods are shown as sets of blocks that specify operations performed but are not necessarily limited to the order or combinations shown for performing the operations by the respective blocks. In portions of the following discussion reference may be made to environment 100 of FIG. 1 and entities detailed in FIGS. 2-8, reference to which is made for example only. The techniques are not limited to performance by one entity or multiple entities operating on one device.

Figure 9:
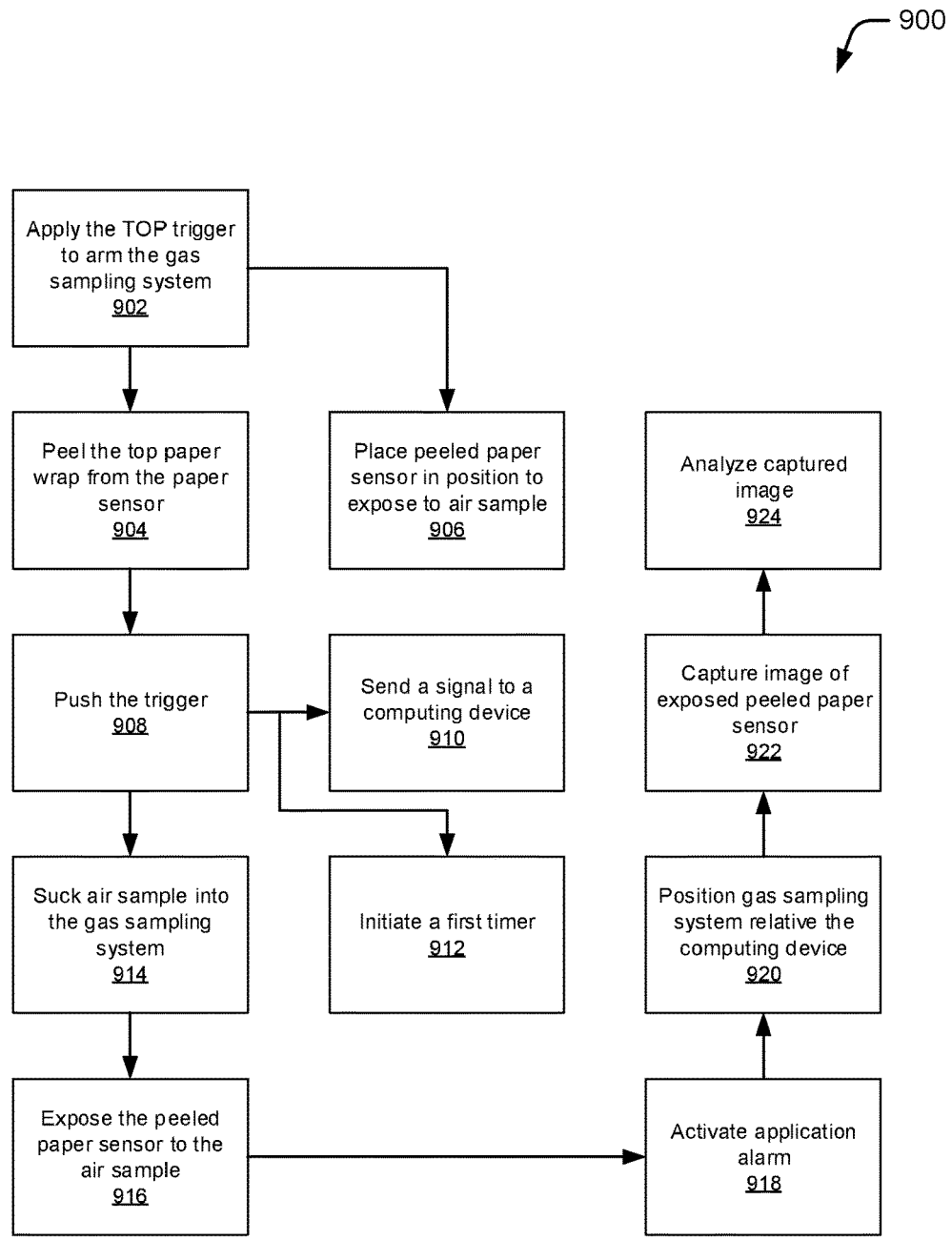
FIG. 9 illustrates a method for using the gas sampling device to ascertain smells in an air sample.

FIG. 9 depicts a method 900, which describes manners in which to use the gas sampling device to ascertain smells in an air sample. In this method, the paper sensors can be routed through the optoelectronic nose 102 in the manner described in relation to FIGS. 5 and 6. Further, in this example the background smells (e.g., those of the surrounding environment) are ignored and the analysis is based solely on the one sample collected.

At 902, a TOP trigger is applied to arm a gas sampling system. For example, a TOP trigger is applied to arm the optoelectronic nose 102. At 904, a top paper wrap is peeled from a paper sensor. For example, the optoelectronic nose 102 peels the paper cover portion 402 from the sensing portion 404 and the back support plastic wrap portion 406. At 906, the peeled paper sensor is placed in position for exposure to an air sample. For example, the optoelectronic nose 102 places the sensing portion 404 on the exposure platform 514 for exposure to an air sample.

At 908, a trigger of the gas sampling system is pushed. For example, a trigger of the optoelectronic nose 102 is pushed. At 910, a signal is sent to a computing device. For example, the optoelectronic nose 102 sends a signal to the computing device 104 via Bluetooth®. At 912, a first timer is initiated. For example, the optoelectronic nose 102 or the computing device 104 initiates a first timer. At 914, an air sample is sucked into the gas sampling system. For example, the optoelectronic nose 102 employs a fan to suck an air sample through the airway 516 into a chamber in which the sensing portion 404 is exposed. At 916, the peeled paper sensor is exposed to the air sample. For example, the sensing portion 404 is exposed to the air sample sucked into the chamber by the fan.

At 918, an application alarm is activated. For example, an alarm for an application of the computing device 102 is activated. At 920 the gas sampling system is positioned relative the computing device. For example, the optoelectronic nose 102 is positioned relative the computing device 104, e.g., the optoelectronic nose 102 is mechanically attached to the computing device 104, magnetically attached, or positioned in other ways as described above in more detail. At 922, an image of the exposed peeled paper sensor is captured. For example, imaging functionality of the computing device 104 is used to capture an image of the sensing portion 404 that was exposed to the air sample at step 916. At 924, the captured image is analyzed to ascertain the smells of the sampled air. For example, the gas sampling manager 210 analyzes the image captured at step 922 to ascertain the smells of the air sample sucked into the optoelectronic nose 102 by the fan at step 914. To do so, the gas sampling manager 210 applies one or more image processing techniques to the images. Results of the analysis are then output. For example, the computing device 104 displays results of the analysis via the display 202.

Figure 10:
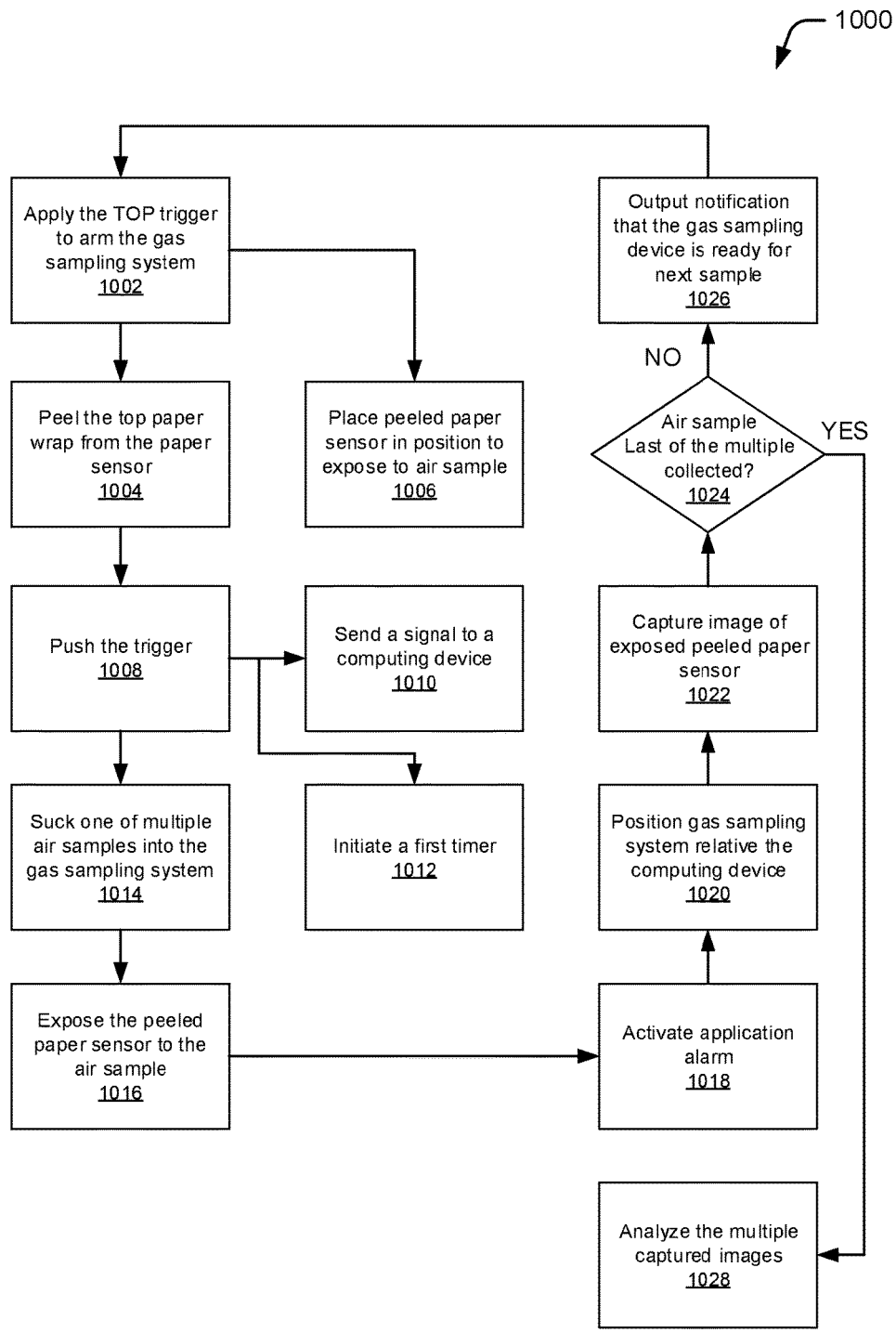
FIG. 10 illustrates a method for using the gas sampling device to ascertain smells in multiple different air samples.

FIG. 10 depicts a method 1000, which describes manners in which to use the gas sampling device to ascertain smells in multiple different air samples. In this method, the paper sensors can again be routed through the optoelectronic nose 102 in the manner described in relation to FIGS. 5 and 6. In contrast to the method described with reference to FIG. 9, however, two samples are collected. First, a surrounding environment air sample or a specimen of interest air sample (e.g., breath) can be collected. Once the first sample is collected, whichever sample was not collected the first time through the process can be collected. For example, if the surrounding air sample was collected the first time through the method, then the specimen of interest air sample can be collected the next time through the method.

At 1002, a TOP trigger is applied to arm a gas sampling system. For example, a TOP trigger is applied to arm the optoelectronic nose 102. At 1004, a top paper wrap is peeled from a paper sensor. For example, the optoelectronic nose 102 peels the paper cover portion 402 from the sensing portion 404 and the back support plastic wrap portion 406. At 1006, the peeled paper sensor is placed in position for exposure to an air sample. For example, the optoelectronic nose 102 places the sensing portion 404 on the exposure platform 514 for exposure to an air sample.

At 1008, a trigger of the gas sampling system is pushed. For example, a trigger of the optoelectronic nose 102 is pushed. At 1010, a signal is sent to a computing device. For example, the optoelectronic nose 102 sends a signal to the computing device 104 via Bluetooth®. At 1012, a first timer is initiated. For example, the optoelectronic nose 102 or the computing device 104 initiates a first timer. At 1014, one of multiple air samples is sucked into the gas sampling system. For example, the optoelectronic nose 102 employs a fan to suck one of the multiple air samples through airway 516 into a chamber in which the sensing portion 404 is exposed. At 1016, the peeled paper sensor is exposed to the air sample. For example, the sensing portion 404 is exposed to the air sample sucked into the chamber by the fan at step 1014.

At 1018, an application alarm is activated. For example, an alarm for an application of the computing device 102 is activated. At 1020 the gas sampling system is positioned relative the computing device. For example, the optoelectronic nose 102 is positioned relative the computing device 104 as described above in more detail. At 1022, an image of the exposed peeled paper sensor is captured. For example, imaging functionality of the computing device 104 is used to capture an image of the sensing portion 404 that was exposed to the air sample at step 1016. At 1024, a determination is made as to whether the air sample collected is the last air sample to be collected. If a determination is made that the air sample that was collected and exposed to the peeled paper sensor is not the last of the samples to be collected, then the method proceeds to step 1026. At 1026, a notification is output that indicates the gas sampling system is ready for a next sample. For example, the computing device 104 outputs a notification via the display 202 that the optoelectronic nose 102 is ready for a next sample. Then the method returns to step 1002 and is repeated for a next sample that is to be collected.

If a determination is made that the air sample that was collected and exposed to the peeled paper sensor is the last of the samples to be collected, however, then the method proceeds to step 1028. At 1028, the multiple captured images are analyzed to ascertain the smells of the sampled air. For example, the gas sampling manager 210 analyzes the images captured at step 1022 at multiple different times to ascertain the smells of the air samples. To do so, the gas sampling manager 210 applies one or more image processing techniques to the images. In this case, the gas sampling manager 210 also ascertains the differences in smells between the different air samples. When one sample corresponds to a specimen sample and another to the surrounding air, for example, the gas sampling manager 210 can subtract the surrounding air smells from the specimen sample smells to ascertain the smells that are unique to the specimen. Results of the analysis are then output. For example, the computing device 104 displays results of the analysis via the display 202.

Figure 11:
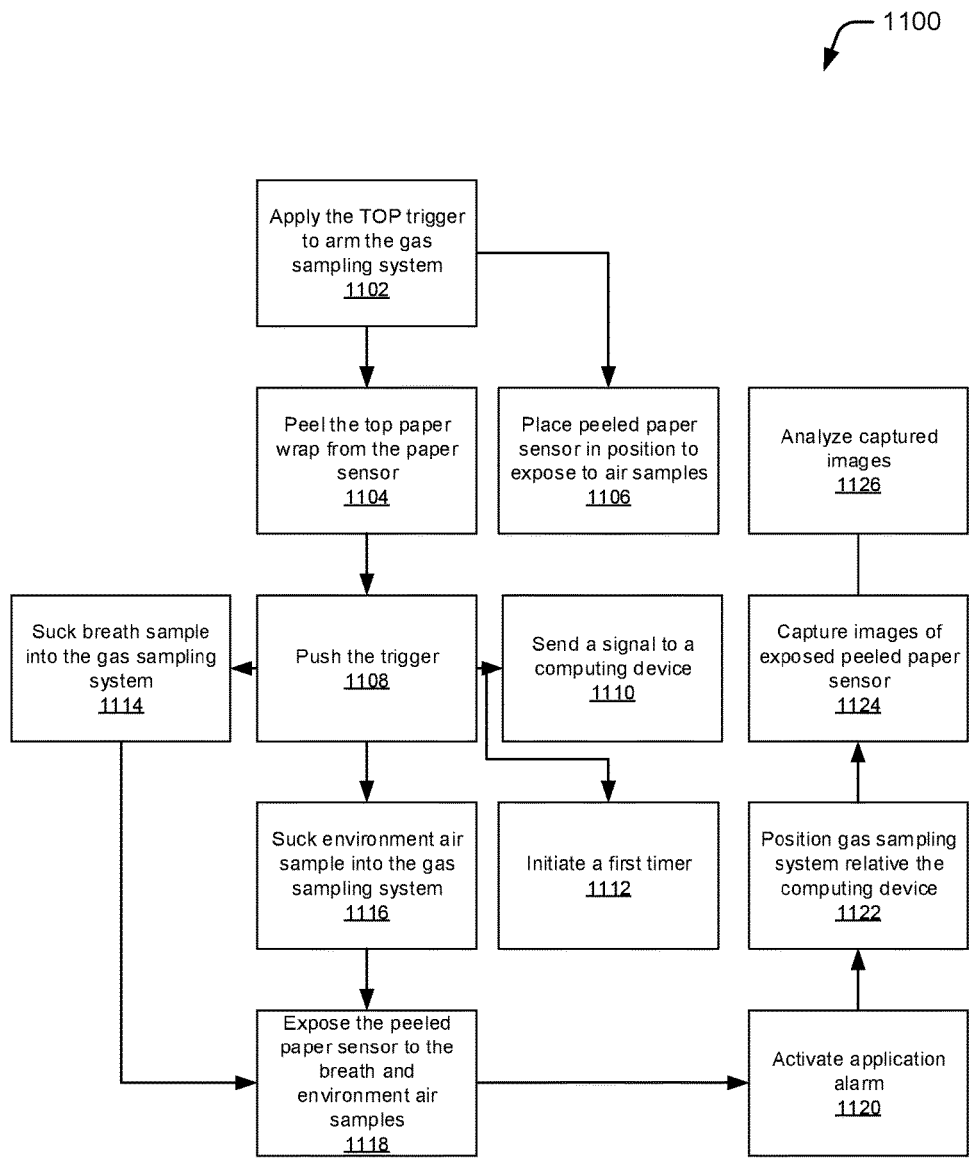
FIG. 11 illustrates a method for using the gas sampling device to ascertain smells in multiple different air samples that are captured at a same time.

FIG. 11 depicts a method 1100, which describes mariners in which to use the gas sampling device to ascertain smells in multiple air samples that are captured at a same time. In this method, the paper sensors can be routed through the optoelectronic nose 102 in the manner described in relation to FIG. 7. Further, in this example the background smells (e.g., those of the surrounding environment) and smells from the specimen of interest are determined by collecting two samples at a same time, e.g., through the two airways 702, 704 of the optoelectronic nose 102 depicted in FIG. 7. In this example, two different rolls of paper sensors can be stored in the sensor housing 302 and exposed to the two samples at the same time—one roll for each sample. Further, the paper cover portion 402 can be disposed in a storage package attached to the optoelectronic nose.

At 1102, a TOP trigger is applied to arm a gas sampling system. For example, a TOP trigger is applied to arm the optoelectronic nose 102. At 1104, a top paper wrap is peeled from a paper sensor. For example, the optoelectronic nose 102 peels the paper cover portion 402 from the sensing portion 404 and the back support plastic wrap portion 406. At 1106, the peeled paper sensor is placed in position for exposure to air samples. For example, the optoelectronic nose 102 places the sensing portion 404 on the exposure platform 514 for exposure to air samples.

At 1108, a trigger of the gas sampling system is pushed. For example, a trigger of the optoelectronic nose 102 is pushed. At 1110, a signal is sent to a computing device. For example, the optoelectronic nose 102 sends a signal to the computing device 104 via Bluetooth®. At 1112, a first timer is initiated. For example, the optoelectronic nose 102 of the computing device 104 initiates a first timer. At 1114, a breath air sample is sucked into the gas sampling system. For example, the optoelectronic nose 102 sucks a breath air sample through airway 704 into a chamber in which the sensing portion 404 is exposed. At 1116, a surrounding environment air sample is sucked into the gas sampling system. For example, the optoelectronic nose 102 sucks an environmental air sample through airway 702 into the chamber in which the sensing portion 404 is exposed. At 1118, the peeled paper sensor is exposed to the breath and environment air samples. For example, the sensing portion 404 is exposed to the breath and surrounding environment air samples sucked into the chamber.

At 1120, an application alarm is activated. For example, an alarm for an application of the computing device 102 is activated. At 1122 the gas sampling system is positioned relative the computing device. For example, the optoelectronic nose 102 is positioned relative the computing device 104 as described above in more detail. At 1124, images of the exposed peeled paper sensor are captured. For example, imaging functionality of the computing device 104 is used to capture images of the sensing portion 404 that was exposed to the breath air sample and the surrounding environment air sample at step 1118. At 1126, the captured images are analyzed to ascertain the smells of the sampled air. For example, the gas sampling manager 210 analyzes the images captured at step 1124 to ascertain the smells of the air samples sucked into the optoelectronic nose 102 at step 1114 and step 1116. To do so, the gas sampling manager 210 applies one or more image processing techniques to the images. In this case, the gas sampling manager 210 also ascertains the differences in smells between the different air samples. When one sample corresponds to a specimen sample, and another to the surrounding air, for example, the gas sampling manager 210 can subtract the surrounding air smells from the specimen sample smells to ascertain the smells that are unique to the specimen. Results of the analysis are then output. For example, the computing device 104 displays results of the analysis via the display 202.

In one or more implementations, the method 1100 of FIG. 11 can be performed using an optoelectronic nose 102 having a sensor housing capable of storing two rolls of paper sensors, but in which a top chamber portion is divided into two zones by a partition. One of the zones is configured as a sealed zone, which in operation is the zone exposed to the air sample from the specimen, and the other zone is configured as an exposed zone, which in operation is the zone in which the paper sensor is subject to the surrounding environment air without external forces on the system. In such implementations, the optoelectronic nose 102 is capable of peeling the two paper sensors at a same time. Further, the paper cover portion 402 of the two paper sensor rolls is disposed in the storage package.

Figure 12:
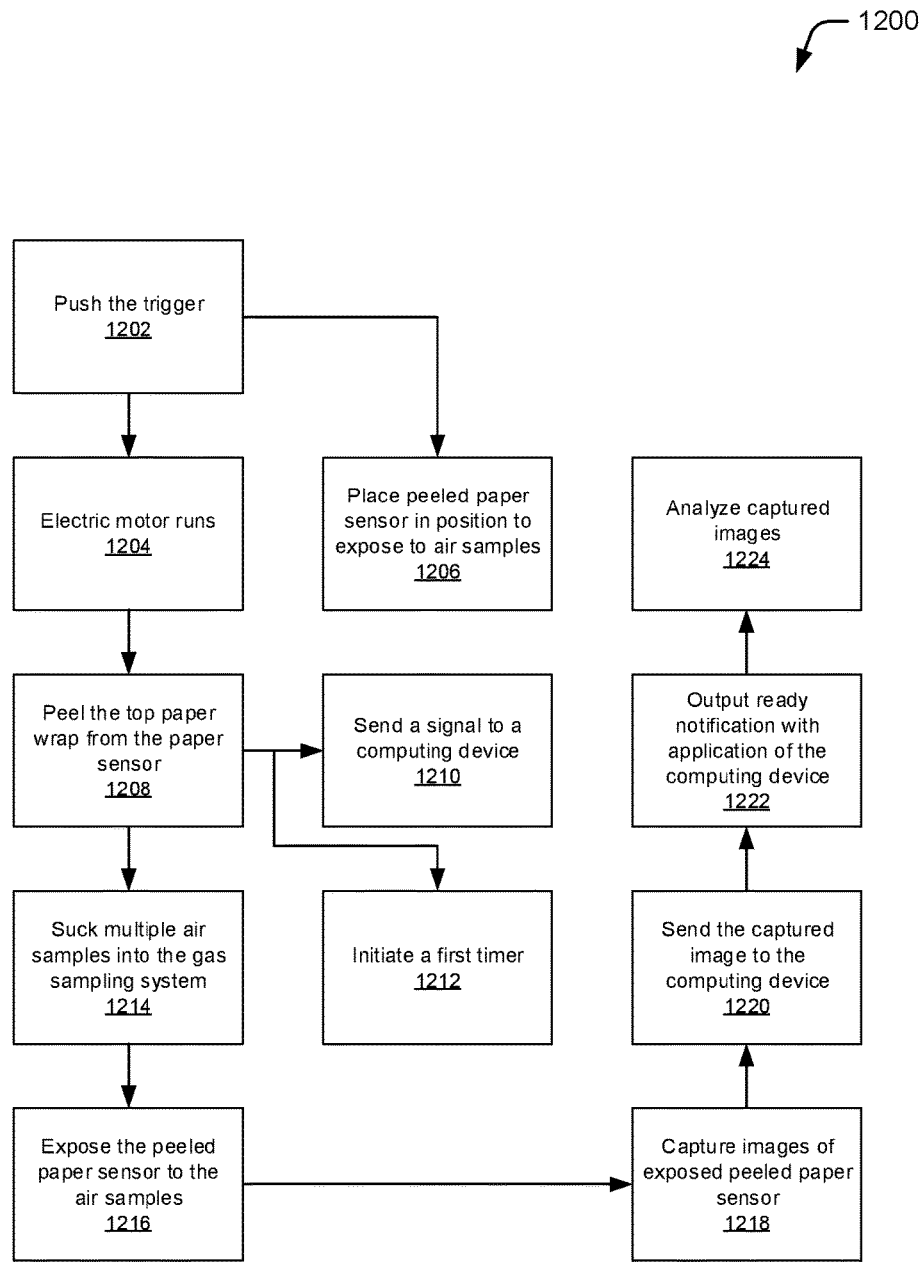
FIG. 12 illustrates another method for using the gas sampling device to ascertain smells in multiple different air samples.

FIG. 12 depicts another method 1200, which describes manners in which to use the gas sampling device to ascertain smells in multiple different air samples. In this method, the optoelectronic nose 102 is configured with a trigger. In response to pushing the trigger, an electric motor of the optoelectronic nose 102 rotates and positions the sensor in position to be exposed to the air that is to be sucked in and also peels the paper cover portion 402 from the paper sensor roll. The paper cover portion 402 can be disposed in the storage package or rolled out of the optoelectronic nose altogether. Two air samples, such as a surrounding environment air sample and a breath air sample, can be sucked into the optoelectronic nose 102 (e.g., through two airways as in FIG. 7). At a certain time, after an exposure time that allows chemical reactions to occur lapses, a camera of the optoelectronic nose 102 will capture an image of the reacted sensing portions 404, which the optoelectronic nose 102 communicates (e.g., via Bluetooth®) to the computing device 104.

At 1202, a trigger of the gas sampling system is pushed. For example, a trigger of the optoelectronic nose 102 is pushed. At 1204, an electric motor is run. For example, an electric motor of the optoelectronic nose 102 is run. At 1206, a paper sensor is placed in position for exposure to air samples. For example, the optoelectronic nose 102 places the example paper sensor 400 of FIG. 4 for exposure to air samples. At 1208, a top paper wrap is peeled from the paper sensor. For example, the optoelectronic nose 102 peels the paper cover portion 402 from the sensing portion 404 and the back support plastic wrap portion 406.

At 1210, a signal is sent to a computing device. For example, the optoelectronic nose 102 sends a signal to the computing device 104 via Bluetooth®. At 1212, a first timer is initiated. For example, the optoelectronic nose 102 or the computing device 104 initiates a first timer. At 1214, a breath air sample and a surrounding environment air sample are sucked into the gas sampling system. For example, the optoelectronic nose 102 sucks a breath air sample through the airway 704 and a surrounding environment air sample through the airway 702 into a chamber in which the sensing portion 404 is exposed. At 1216, the peeled paper sensor is exposed to the breath and environment air samples. For example, the sensing portion 404 is exposed to the breath and surrounding environment air samples sucked into the chamber.

At 1218, images of the exposed peeled paper sensor are captured. For example, imaging functionality of the optoelectronic nose 102 is used to capture images of the sensing portion 404 that was exposed to the breath air sample and the surrounding environment air sample at step 1216. At 1220, the captured images are sent to the computing device. For example, the optoelectronic nose 102 sends the images captured at step 1218 to the computing device 104 via Bluetooth®. At 1222, a ready notification is output with an application of the computing device. For example, an application of the computing device 104 causes a ready notification to be output via the display 202. In one or more implementations the notification from the application indicates it is ready to take the breath air sample by selecting the application (e.g., via the display 202 of the computing device). A user can then move the optoelectronic nose 102 near their breath so that the breath can be captured as well. The process of capturing the image of the breath on the paper sensor can then be performed again. At 1224, the captured images are analyzed to ascertain the smells of the sampled air. For example, the gas sampling manager 210 analyzes the images captured at step 1218 to ascertain the smells of the air samples sucked into the optoelectronic nose 102 at step 1214. To do so, the gas sampling manager 210 applies one or more image processing techniques to the images. In this case, the gas sampling manager 210 also ascertains the differences in smells between the different air samples. When one sample corresponds to a specimen sample, and another to the surrounding air, for example, the gas sampling manager 210 can subtract the surrounding air smells from the specimen sample smells to ascertain the smells that are unique to the specimen. Results of the analysis are then output. For example, the computing device 104 displays results of the analysis via the display 202.

The preceding discussion describes methods relating to gas sampling device techniques. Aspects of these methods may be implemented in hardware (e.g., fixed logic circuitry), firmware, software, manual processing, or any combination thereof. These techniques may be embodied on one or more of the entities shown in FIGS. 1-8, and 13 (computing system 1300 is described in FIG. 13 below), which may be further divided, combined, and so on. Thus, these figures illustrate some of the many possible systems or apparatuses capable of employing the described techniques. The entities of these figures generally represent software, firmware, hardware, whole devices or networks, or a combination thereof.

Example Computing System

Figure 13:
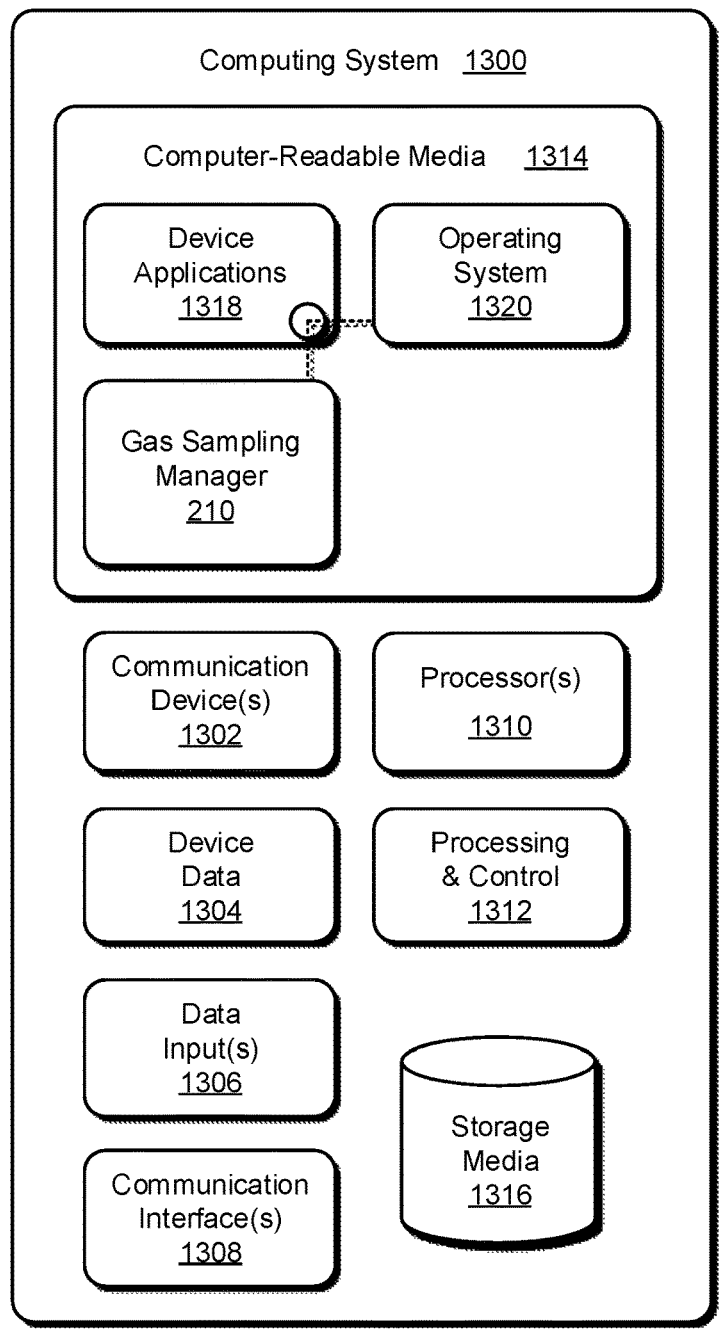
FIG. 13 illustrates an example computing system embodying, or in which techniques may be implemented that enable use of, a gas sampling device.

FIG. 13 illustrates various components of example computing system 1300 that can be implemented as any type of client, server, and/or computing device as described with reference to the previous FIGS. 1-12 to implement gas sampling device techniques. In embodiments, the computing system 1300 can be implemented as one or a combination of a wired and/or wireless wearable device, System-on-Chip (SoC), and/or as another type of device or portion thereof. The computing system 1300 may also be associated with a user (e.g., a person) and/or an entity that operates the device such that a device describes logical devices that include users, software, firmware, and/or a combination of devices.

The computing system 1300 includes communication devices 1302 that enable wired and/or wireless communication of device data 1304 (e.g., received data, data that is being received, data scheduled for broadcast, data packets of the data, etc.). The device data 1304 or other device content can include configuration settings of the device, media content stored on the device, and/or information associated with a user of the device. Media content stored on the computing system 1300 can include any type of audio, video, and/or image data, including complex or detailed results of gas sampling device techniques. The computing system 1300 includes one or more data inputs 1306 via which any type of data, media content, and/or inputs can be received, such as human utterances, user-selectable inputs (explicit or implicit), messages, music, television media content, recorded video content, and any other type of audio, video, and/or image data received from any content and/or data source.

The computing system 1300 also includes communication interfaces 1308, which can be implemented as any one or more of a serial and/or parallel interface, a wireless interface, any type of network interface, a modem, and as any other type of communication interface. The communication interfaces 1308 provide a connection and/or communication links between the computing system 1300 and a communication network by which other electronic, computing, and communication devices communicate data with the computing system 1300.

The computing system 1300 includes one or more processors 1310 (e.g., any of microprocessors, controllers, and the like), which process various computer-executable instructions to control the operation of the computing system 1300 and to enable techniques for, or in which can be embodied, gas sampling device techniques. Alternatively or in addition, the computing system 1300 can be implemented with any one or combination of hardware, firmware, or fixed logic circuitry that is implemented in connection with processing and control circuits which are generally identified at 1312. Although not shown, the computing system 1300 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

The computing system 1300 also includes computer-readable media 1314, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. The computing system 1300 can also include a mass storage media device 1316.

The computer-readable media 1314 provides data storage mechanisms to store the device data 1304, as well as various device applications 1318 and any other types of information and/or data related to operational aspects of the computing system 1300. For example, an operating system 1320 can be maintained as a computer application with the computer-readable media 1314 and executed on the processors 1310. The device applications 1318 may include a device manager, such as any form of a control application, software application, signal-processing and control module, code that is native to a particular device, a hardware abstraction layer for a particular device, and so on.

The device applications 1318 also include any system components, engines, or managers to implement the techniques. In this example, the device applications 1318 include the gas sampling manager 210.

CONCLUSION

Although embodiments of techniques using, and apparatuses enabling, a gas sampling system have been described in language specific to features and/or methods, it is to be understood that the subject of the appended claims is not necessarily limited to the specific features or methods described. Rather, the specific features and methods are disclosed as example implementations of these techniques.

What is claimed is:

1. A method for ascertaining smells from air samples, the method comprising:
    exposing a thin film sensing portion of a gas sampling sensor within an optoelectronic nose, the thin film sensing portion reacting chemically when exposed to air samples;
    positioning the thin film sensing portion of the gas sampling sensor in a chamber of the optoelectronic nose for exposure to one or more air samples;
    obtaining the one or more air samples in the chamber through one or more airways of the optoelectronic nose to expose the thin film sensing portion of the gas sampling sensor to the one or more air samples;
    after an exposure time that allows chemical reactions to occur between the thin film sensing portion and the one or more air samples, capturing one or more images of the thin film sensing portion that is exposed to, and chemically reacts with, the one or more air samples using a camera associated with the optoelectronic nose;
    applying one or more image processing techniques to the one or more images to ascertain the smells of the one or more air samples; and
    outputting an indication of the ascertained smells.

2. A method as recited in claim 1, wherein:
two air samples, comprising an environment air sample and a specimen of interest air sample, are obtained in the chamber to expose the thin film sensing portion of the gas sampling sensor to the environment air sample and the specimen of interest air sample;
at least two images are captured of the thin-film sensing portion, one of the at least two images corresponding to the environment air sample and another of the at least two images corresponding the specimen of interest air sample; and
the one or more image processing techniques are applied to the at least two images to ascertain differences in smells between the environment air sample and the specimen of interest air sample.

3. A method as recited in claim 2, further comprising ascertaining the smells that are unique to the specimen of interest air sample based on the differences in smells between the environment air sample and the specimen of interest air sample.

4. A method as recited in claim 2, wherein the differences in smells between the environment air sample and the specimen of interest air sample are ascertained by subtracting the smells of the environment air sample from the smells of the specimen of interest air sample.

5. A method as recited in claim 1, further comprising calibrating the optoelectronic nose by ascertaining the smells of an environment air sample before ascertaining the smells of the one or more air samples.

6. A method as recited in claim 1, further comprising communicating the one or more images of the thin film sensing portion to a computing device configured to apply the one or more image processing techniques to ascertain the smells of the one or more air samples and output the indication of the ascertained smells.

7. A method as recited in claim 1,
wherein capturing the one or more images using the camera positions a computing device having the camera relative to the optoelectronic nose to enable the camera to capture the one or more images of the thin film sensing portion that is exposed to the one or more air samples.

8. A method as recited in claim 7, wherein the computing device applies the one or more image processing techniques to the one or more images to ascertain the smells of the one or more air samples and outputs the indication of the ascertained smells.

9. A method as recited in claim 1, wherein exposing the thin film sensing portion of the gas sampling sensor comprises peeling a cover portion of the gas sampling sensor away from the thin film sensing portion.

10. A system to ascertain smells from air samples, the system comprising:
a chamber in which a thin film gas sampling sensor is positioned for exposure to one or more air samples, the gas sampling sensor configured to react chemically when exposed to air samples;
one or more airways through which the one or more air samples are obtained in the chamber to expose the gas sampling sensor to the one or more air samples; and
a communication device to communicate an indication to a computing device to ascertain smells of the one or more air samples from one or more images, the one or more images captured by a camera associated with the system after an exposure time that allows chemical reactions to occur between the one or more air samples and the thin film gas sampling sensor.

11. A system as recited in claim 10, wherein the thin film gas sampling sensor is a paper sensor comprising at least a paper cover portion and a sensing portion, and the thin film gas sampling sensor is positioned for exposure to the one or more air samples, in part, by peeling the paper cover portion away from the sensing portion.

12. A system as recited in claim 11, wherein the paper sensor is part of a roll of paper sensors, and the thin film gas sampling sensor is positioned for exposure to the one or more air samples, in part, by unrolling the roll of paper sensors.

13. A system as recited in claim 10, wherein the thin film gas sampling sensor is a chip sensor configured to react chemically when exposed to air samples.

14. A system as recited in claim 10, wherein the camera associated with the system is associated through an attachment to attach the computing device in a position relative to the chamber that enables the camera of the computing device to capture the one or more images of the thin film gas sampling sensor.

15. A system as recited in claim 10, further comprising:
a light shielding box to control light to which the thin film gas sampling sensor is exposed; and
a light delivery implement to expose the thin film gas sampling sensor to one or more types of light in connection with capturing the one or more images of the thin film gas sampling sensor.

16. A device comprising
a camera to capture images of a thin film gas sampling sensor that is positioned in an optoelectronic nose for exposure to air samples;
one or more processors; and
memory having stored thereon computer-readable instructions that are executable by the one or more processors and programmed to perform operations comprising:
responsive to receiving an indication to ascertain smells of one or more air samples to which the thin film gas sampling sensor is exposed, utilizing the camera to capture one or more images of the thin film gas sampling sensor, the one or more images capturing characteristics of chemical reactions between the thin film gas sampling sensor and the one or more air samples;
applying one or more image processing techniques to the one or more images to ascertain the smells of the one or more air samples, the one or more image processing techniques matching the characteristics captured in the one or more images to patterns that are indicative of the smells of the one or more air samples; and
outputting an indication of the ascertained smells.

17. A device as recited in claim 16, wherein the operations further comprise:
utilizing the camera to capture at least two images of the thin film gas sampling sensor that correspond to two air samples, including an environment air sample and a specimen of interest air sample; and
applying the one or more image processing techniques to the at least two different images to ascertain differences in smells between the environment air sample and the specimen of interest air sample.

18. A device as recited in claim 16, wherein the camera is configured to capture, in the one or more images, infrared or ultraviolet information, and applying the one or more image processing techniques to the one or more images to ascertain the smells of the one or more air samples includes analyzing the infrared or ultraviolet information within the one or more images.

19. A method as recited in claim 1, wherein the one or more image processing techniques analyze non-visual information within the one or more images.

20. A method as recited in claim 19, wherein the non-visual information includes infrared information and the one or image processing techniques analyze the infrared information of the one or more images to determine a heat omitted by the thin film sensing portion, the heat omitted indicative of a chemical reaction.

* * * * *

UNITED STATES PATENT AND TRADEMARK OFFICE
CERTIFICATE OF CORRECTION

PATENT NO. : 10,088,462 B2  
APPLICATION NO. : 15/274950  
DATED : October 2, 2018  
INVENTOR(S) : Houtan Neynavaee, Stephen Theodore Schooley and Sam Kavusi Page 1 of 1

It is certified that error appears in the above-identified patent and that said Letters Patent is hereby corrected as shown below:

In the Claims

Column 18, Line 29, after "device" before "a" delete "comprising" and insert --comprising:--

Signed and Sealed this
Twentieth Day of November, 2018

Andrei Iancu
*Director of the United States Patent and Trademark Office*